United States Patent
Ismail

(10) Patent No.: US 10,881,589 B2
(45) Date of Patent: Jan. 5, 2021

(54) BARIATRIC DEVICE AND METHOD

(71) Applicant: CapsForAll, LLC, Nashville, TN (US)

(72) Inventor: Muhammad Sami Ismail, Nashville, TN (US)

(73) Assignee: CapsForAll, LLC, Nashville, TN (US)

( * ) Notice: Subject to any disclaimer, the term of this patent is extended or adjusted under 35 U.S.C. 154(b) by 285 days.

(21) Appl. No.: 15/940,059

(22) Filed: Mar. 29, 2018

(65) Prior Publication Data

US 2019/0099331 A1   Apr. 4, 2019

Related U.S. Application Data

(63) Continuation of application No. 14/750,026, filed on Jun. 25, 2015, now abandoned.

(60) Provisional application No. 62/016,921, filed on Jun. 25, 2014.

(51) Int. Cl.
  *A61J 15/00*   (2006.01)
  *A61F 5/00*   (2006.01)

(52) U.S. Cl.
  CPC ......... *A61J 15/0049* (2013.01); *A61F 5/0013* (2013.01); *A61F 5/0076* (2013.01); *A61J 15/0015* (2013.01); *A61J 15/0069* (2013.01); *A61J 15/0073* (2013.01)

(58) Field of Classification Search
  CPC ............... A61J 15/0049; A61J 15/0015; A61J 15/0069; A61J 15/0073; A61M 5/0076; A61M 5/0013
  See application file for complete search history.

(56) References Cited

U.S. PATENT DOCUMENTS

| | | | |
|---|---|---|---|
| 3,411,506 A | 11/1968 | Velasco | |
| 4,100,246 A | 7/1978 | Frisch | |
| 4,543,089 A | 9/1985 | Moss | |
| 4,668,225 A * | 5/1987 | Russo | A61J 15/0015 604/104 |
| 5,071,405 A * | 12/1991 | Piontek | A61J 15/0015 604/103.03 |
| 5,314,409 A | 5/1994 | Sarosiek et al. | |
| 5,318,530 A | 6/1994 | Nelson, Jr. | |
| 5,709,657 A | 1/1998 | Zimmon | |

(Continued)

FOREIGN PATENT DOCUMENTS

| | | |
|---|---|---|
| CN | 202387090 U | 8/2012 |
| WO | 2011/004335 A2 | 1/2011 |

OTHER PUBLICATIONS

International Search Report and Written Opinion received for PCT Patent Application No. PCT/US2015/037680, dated Sep. 29, 2015, 11 pages.

*Primary Examiner* — Philip R Wiest
(74) *Attorney, Agent, or Firm* — Greenspoon Marder LLP; Justin F. McNaughton

(57) ABSTRACT

A bariatric device and procedure configured to control the amount of food and nutrients entering a person's duodenum and reduce the weight of the person, in one aspect, comprises a gastrostomy tube having a proximal end and a distal end; a feeding tube assembly, said assembly including a feeding tube having a proximal end and a distal end; a gastrostomy tube anchor for securing the distal end of said gastrostomy tube inside the stomach; and a first feeding tube anchor designed to be expanded after the pyloric sphincter so as to anchor the distal end of said feeding tube in the duodenum.

22 Claims, 7 Drawing Sheets

(56) References Cited

U.S. PATENT DOCUMENTS

| | | | |
|---|---|---|---|
| 6,997,909 B2 | 2/2006 | Goldberg | |
| 7,220,253 B2 | 5/2007 | Kantsevoy et al. | |
| 7,470,251 B2 | 12/2008 | Shah | |
| 7,721,742 B2 | 5/2010 | Kalloo et al. | |
| 7,740,624 B2 | 6/2010 | Klein et al. | |
| 7,819,840 B2 | 10/2010 | Burnside et al. | |
| 8,529,612 B2 | 9/2013 | Singh | |
| 2004/0034320 A1 | 2/2004 | Burnett | |
| 2005/0215959 A1 | 9/2005 | Whitington | |
| 2006/0129124 A1* | 6/2006 | Kantsevoy | A61J 15/0015 604/509 |
| 2006/0276746 A1* | 12/2006 | Burnside | A61M 25/10 604/103 |
| 2015/0374587 A1 | 12/2015 | Ismail | |

* cited by examiner

BARIATRIC DEVICE AND METHOD

CROSS-REFERENCE TO RELATED APPLICATION

This application is a continuation of U.S. application Ser. No. 14/750,026, filed 25 Jun. 2015, which claims benefit under 35 U.S.C. § 119(e) of U.S. Provisional Application No. 62/016,921, filed 25 Jun. 2014, the contents of which are incorporated herein by reference in their entirety.

TECHNICAL FIELD

The disclosure relates generally to a bariatric device and method. More specifically, the disclosure is directed to a combination trans-abdominal feeding and stomach aspirating device and methods of use for weight loss and obesity treatment.

BACKGROUND

The information provided below is not admitted to be prior art to the present invention, but is provided solely to assist the understanding of the reader.

Obesity is a major public health issue in the United States. The obesity rate in the United States is among the highest in the world as one out of every three Americans is now considered obese. Obesity has led to over approximately 120,000 preventable deaths and has been cited as a contributing factor to another estimated 100,000-400,000 annual deaths in the United States. Unfortunately, many Americans are unable to or do not adequately control their weight and require medical intervention to lose weight, while many others desire to lose weight for various aesthetic reasons.

Numerous medical devices and surgical procedures for cosmetic weight reduction and the treatment of obesity have been proposed. Gastric bypass procedures are one of the most commonly employed bariatric surgeries in the United States. These procedures typically involve the division of the stomach into a small pouch and a large pouch, and resection or rerouting of the small intestines to the small pouch to limit the volume of food a person can consume before reaching satiation; the theory being that the smaller the useable stomach volume, the lower the calories that can be absorbed by the body. Other options include sleeve gastrectomy and gastric banding surgery, which generally involve surgical removal of a large portion of the stomach or mechanical reduction of the size of the stomach, respectively. Still yet other options include direct, controlled feeding into the gastrointestinal tract using an enteral feeding tube alone or in conjunction with an aspirating device for removing excess food from the stomach. For example, one such device is disclosed in U.S. Pat. No. 4,543,089.

However, existing weight reduction devices and procedures are very invasive, have considerable recovery times, often cause nutritional deficiencies, and offer only limited success because they do not cause the subject to permanently change his or her eating habits. In addition, trans-abdominal gastrointestinal feeding and aspirating devices and procedures are prone to clogging by particulate and solid foods and so limit the volume and consistency of food that can be eaten and removed from the stomach. Moreover, such devices can become dislodged easily and cannot be readily adjusted or accessed.

Therefore, a need exists for an improved trans-abdominal bariatric device and procedure that can control the amount of food and nutrients passing out of a person's stomach to the duodenum and permit the removal of excess food from the stomach. In addition, what is needed is an easy to install, minimally invasive bariatric device which may be adjusted or replaced and which will not easily become dislodged from a person's stomach. It is also an object of the present disclosure to provide a bariatric device having a minimal number of separate tubes and or parts inside a person's body. Other objects and advantages will become apparent from the following disclosure.

SUMMARY

The present disclosure provides devices and methods for reducing the weight of overweight and obese individuals. More specifically, the disclosure provides bariatric devices and procedures for simultaneously facilitating weight loss and improving healthy eating behaviors while delivering proper nutrition to a person.

In one aspect of the disclosure, a bariatric device comprises: a gastrostomy tube having a proximal end and a distal end; a feeding tube assembly (optionally at least partially nested within said gastrostomy tube), said assembly including a feeding tube having a proximal end and a distal end; a gastrostomy tube anchor attached to said gastrostomy tube and designed to be expanded inside a person's stomach at the stomach wall to secure the distal end of said gastrostomy tube inside the stomach; and a first feeding tube anchor attached to said feeding tube assembly, said first feeding tube anchor designed to be expanded inside a person's pyloric sphincter (i.e. positioned and expanded beyond/after the pyloric sphincter, within the intestine) so as to secure the distal end of the feeding tube in a person's duodenum. Advantageously, both the gastrostomy tube and feeding tube of the bariatric device can be secured/anchored within a patient, which significantly reduces the chances of the tubes becoming dislodged in a person's stomach. Furthermore, the use of independent anchors for the gastrostomy tube and feeding tube assembly allows the tubes to be manipulated individually, permitting simple and minimally invasive removal and replacement of device components (for example, it is possible for the gastrostomy tube to be removed and replaced whilst the feeding tube remains anchored in position, and vice versa).

Optionally, the gastrostomy tube anchor is a gastrostomy balloon which is designed to be inflated inside a person's stomach. Optionally, the first feeding tube anchor is a first feeding tube balloon designed to be inflated inside/after a person's pyloric sphincter, and the feeding tube assembly includes a first balloon inflation tube, wherein the first feeding tube balloon is in communication with said first balloon inflation tube.

Optionally, the bariatric device further comprises a second feeding tube anchor attached to said feeding tube assembly, designed to be positioned and expanded outside/before the pyloric sphincter so as to secure the distal end of the feeding tube in a person's duodenum in conjunction with said first feeding tube anchor. In such embodiments, the second feeding tube anchor may be a second feeding tube balloon designed to be positioned and inflated before a person's pyloric sphincter, and the feeding tube assembly optionally includes a second balloon inflation tube, wherein the second feeding tube balloon is in communication with said second balloon inflation tube.

The bariatric device may comprise: a gastrostomy tube having a proximal end and a distal end; a feeding tube assembly at least partially nested within said gastrostomy tube, said assembly including a feeding tube having a proximal end and a distal end, and first and second balloon inflation tubes; a gastrostomy balloon attached to said gastrostomy tube and designed to be inflated inside a person's stomach at the stomach wall to anchor the distal end of said gastrostomy tube inside the stomach; and first and second feeding tube balloons in communication with said first and second balloon inflation tubes, said first balloon designed to be inflated inside a person's pyloric sphincter and said second balloon designed to be inflated outside a person's pyloric sphincter so as to anchor the distal end of the feeding tube in a person's duodenum. Using first and second feeding tube balloons which can be inflated on either side of a person's pyloric sphincter allows both forwards and backwards motion of the feeding tube through the pyloric sphincter to be restricted, and thus provides a way of securing the feeding tube at a desired position within the duodenum.

In another aspect of the disclosure, the invention provides a feeding tube device, comprising a feeding tube assembly and feeding tube anchor(s) as described herein. For example, the feeding tube device comprises: a feeding tube having a proximal end and a distal end, a first balloon inflation tube, and a first feeding tube balloon in communication with said first balloon inflation tube, said first balloon designed to be inflated after a person's pyloric sphincter so as to anchor the distal end of said feeding tube in a person's duodenum. In such embodiments, the feeding tube device may further comprise a second feeding tube balloon, wherein the first and second feeding tube balloons are designed to be inflated on either side of a person's pyloric sphincter so as to anchor the distal end of said feeding tube in a person's duodenum. In such embodiments, the feeding tube device suitably includes a second balloon inflation tube, and the second feeding tube balloon is in communication with said second balloon inflation tube.

In another aspect of the disclosure, a gastrostomy tube comprises a proximal and a distal end, a sidewall, and a tube support channel on or in the sidewall for receiving a feeding tube assembly, and further comprising a gastrostomy tube anchor attached to said gastrostomy tube and designed to be expanded inside a person's stomach at the stomach wall to secure the distal end of said gastrostomy tube inside the stomach.

In another aspect of the disclosure, a kit of parts for constructing a bariatric device as described herein comprises a gastrostomy tube and a feeding tube assembly as described herein.

In another aspect of the disclosure, a method for reducing the weight of a person comprises installing a bariatric device disclosed herein in said person's stomach and limiting the amount of food that passes the stomach into the duodenum using said device to evacuate orally consumed food and directly deposit nutrition to the person's intestinal tract downstream of the stomach.

In another aspect of the disclosure, the present invention provides a method for reducing the weight of a person for cosmetic (i.e. non-therapeutic) purposes using a bariatric device disclosed herein, the method comprising limiting the amount of food that passes the stomach into the duodenum using said device to evacuate orally consumed food and directly deposit nutrition to the person's intestinal tract downstream of the stomach.

In another aspect of the disclosure, a method for delivering nutrients to a person comprises installing a bariatric device disclosed herein in said person's stomach and using said device to evacuate orally consumed food and directly deposit nutrition to the person's intestinal tract downstream of the stomach.

In another aspect of the disclosure, a method for installing a bariatric device as disclosed herein in a person, comprises (i) inserting said gastrostomy tube into the person's stomach and securing the gastrostomy tube in place by expanding said gastrostomy tube anchor (e.g. inflating a gastrostomy balloon); and (ii) inserting said feeding tube assembly through the person's stomach into the duodenum and securing said feeding tube in place by expanding said first feeding tube anchor after the pyloric sphincter (e.g. inflating a first feeding tube balloon after the pyloric sphincter).

In another aspect of the disclosure, a method for replacing a gastrostomy tube as described herein with a replacement gastrostomy tube as described herein, comprises (i) retracting said gastrostomy tube anchor and removing said gastrostomy tube and (ii) inserting a replacement gastrostomy tube and expanding the gastrostomy tube anchor of the replacement gastrostomy tube.

In another aspect of the disclosure, a method for replacing a feeding tube assembly as described herein with a replacement feeding tube assembly as described herein, comprises (i) retracting said first feeding tube anchor (and, if present, retracting said second feeding tube anchor) and removing said feeding tube assembly and (ii) inserting a replacement feeding tube assembly and expanding the first feeding tube anchor (and, if present, expanding said second feeding tube anchor) of the replacement feeding tube assembly.

These and other aspects and advantages of the invention described herein will be better understood and appreciated by those skilled in the art by reference to the accompanying drawings briefly described below in conjunction with the following detailed description, wherein certain preferred embodiments including the best mode are described. It is to be understood that the specific devices and processes illustrated in the attached drawings and described in the following detailed description are exemplary embodiments of the inventive concepts defined in the claims below. Hence, specific dimensions and other physical characteristics relating to the embodiments disclosed herein are to be regarded as illustrative in nature and not as restrictive, unless the claims expressly state otherwise.

DETAILED DESCRIPTION

Figure 1A:
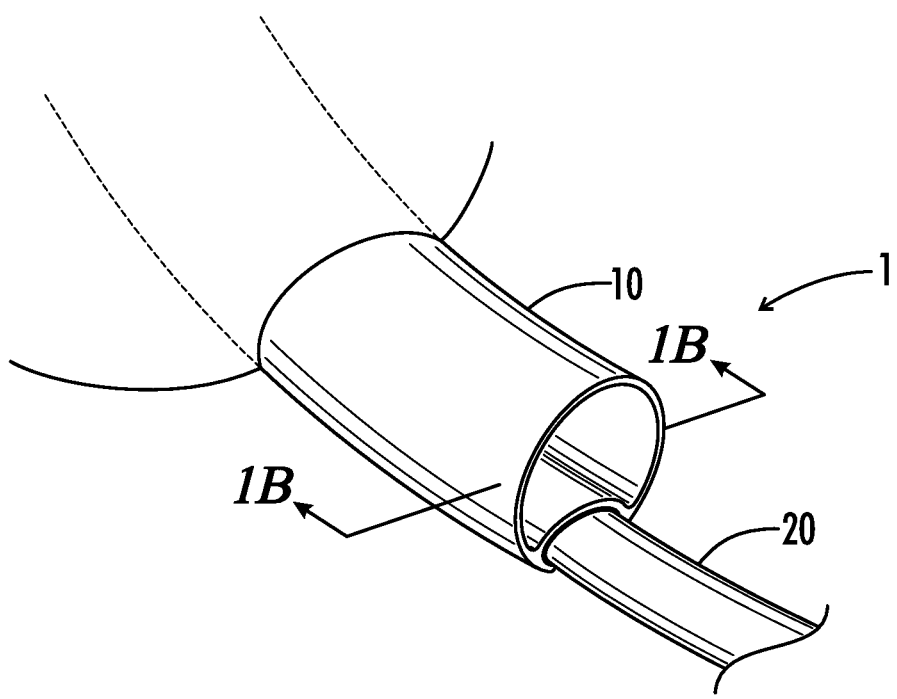
FIG. 1A is a perspective view of a trans-abdominal bariatric device constructed in accordance with the teachings of the present disclosure.

The following detailed description is presented to enable one of ordinary skill in the art to make and use the invention and to incorporate it in the context of particular applications. It is to be understood that the specific devices and processes illustrated in the attached drawings and described in the following specification are exemplary embodiments of the inventive concepts defined in the claims below. Various modifications, as well as a variety of uses in different applications, will be readily apparent to those skilled in the art. Thus, specific dimensions and other physical characteristics relating to the embodiments disclosed herein are not to be considered as limiting, unless the claims expressly state otherwise and the invention is not intended to be limited to the embodiments presented, but is to be accorded the widest scope consistent with the principles and novel features disclosed herein.

The present disclosure provides means and methods for safely inducing weight loss in overweight and obese individuals. The means and methods disclosed herein provide an easy-to-use, trans-abdominal bariatric device and procedure for strictly controlling the amount of food and nutrition entering a person's gastrointestinal tract that do not require rescission or rerouting of the person's organs or tissues. The bariatric device disclosed herein is designed to be inserted through the abdominal and stomach walls and generally comprises a feeding tube assembly slidably nested within a larger gastrostomy tube. The device can be installed in a subject with minimal surgery and requires minimal recovery time. In general, the gastrostomy tube is inserted and anchored in the stomach by an inflatable balloon, while a terminal end of the feeding tube that protrudes from the gastrostomy tube is inserted and anchored in the duodenum by an inflatable balloon positioned after the pyloric sphincter, or by two inflatable balloons positioned on either side of the pyloric sphincter. Due to the large diameter of the gastrostomy tube, the bariatric device will be much less likely to clog when used to evacuate ground foods from the stomach.

Optionally, the feeding tube assembly is at least partially nested within the gastrostomy tube. By "at least partially nested within the gastrostomy tube" we mean that at least a part of the feeding tube assembly is positioned within the gastrostomy tube, for example, in the interior of the gastrostomy tube or inset into a sidewall of the gastrostomy tube. The feeding tube assembly may be accommodated in a tube support channel/track/slot provided on or in the sidewall of the gastrostomy tube, preferably such that the feeding tube can slide relative to the gastrostomy tube within the tube support channel. In such embodiments, the tube support channel may extend along more than 10%, more than 20%, more than 30%, more than 40%, more than 50%, more than 60%, more than 70%, more than 80% or more than 90% of the gastrostomy tube. Advantageously, accommodating the feeding tube assembly within a tube support channel extending along the gastrostomy tube restricts lateral movement of the feeding tube assembly, thus reducing the propensity of the feeding tube to become dislodged from the duodenum. Such a tube support channel may be in an interior sidewall of the gastrostomy tube, or may be in an exterior sidewall of the gastrostomy tube. The tube support channel may open onto the interior of the gastrostomy tube, or may open to the exterior of the gastrostomy tube. The gastrostomy tube includes an aspirating channel/lumen for aspirating material from a patient's stomach. In embodiments in which the gastrostomy tube includes a tube support channel, the tube support channel may be separate from the aspirating channel.

Turning now to the drawings, wherein like reference numbers refer to like elements, FIG. 1A depicts an exemplary trans-abdominal bariatric device 1 constructed in accordance with the present disclosure. The bariatric device 1 comprises a gastro-duodenal feeding tube assembly 20 nested at least partially inside a larger diameter, generally hollow gastrostomy tube 10, and at least two balloons. In one embodiment, the device comprises three balloons. The balloons are made of medical grade materials standard to the industry and compliant with medical standards, such as silicone. The diameter of the gastrostomy tube may range from 0.5 cm to 5.0 cm, for example, 0.5 cm to 4.0 cm, 0.5 cm to 3.0 cm, 1.0 cm to 2.5 cm, or 1.5 to 2.5 cm. In some embodiments, the diameter of the gastrostomy tube is approximately 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, or 5.0 centimeters. In one embodiment, the gastrostomy tube is approximately 2.0 cm. The large diameter of the gastrostomy tube 10 facilitates the evacuation of thick, high consistency or high viscosity foods, including ground solid foods.

Figure 1B:
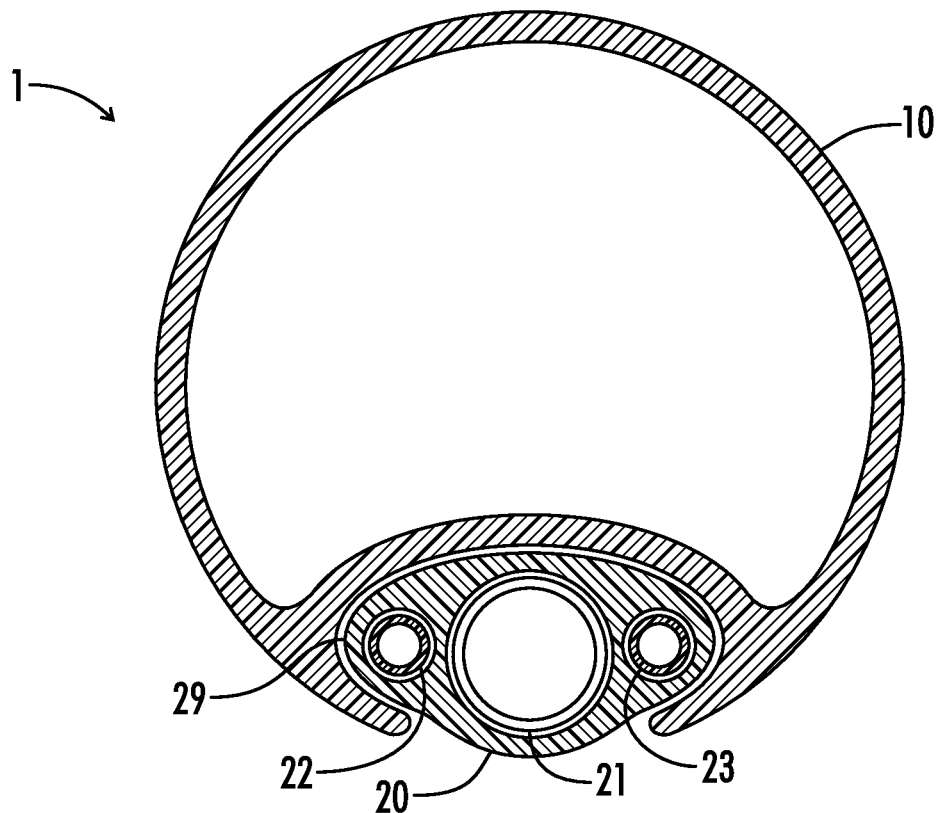
FIG. 1B is a cross section diagram of the bariatric device of FIG. 1A.

As shown in FIG. 1B the feeding tube assembly 20 comprises a hollow feeding tube 21 and two hollow balloon inflation tubes 22, 23, held with channels running along the feeding tube assembly. In other embodiments the feeding tube and hollow balloon inflation tubes may be integrally formed as part of the feeding tube assembly, i.e. the feeding tube and first and second balloon inflation tubes may be individual lumens formed as part of the feeding tube assembly body. In one embodiment, the feeding tube assembly has at least one balloon in communication therewith. The feeding tube assembly 20 can be inset or nested in and running parallel to an outside wall of the gastrostomy tube 10. In the embodiment shown, the outer wall of the gastrostomy tube 10 contains a tube support channel having a space 29 and overhanging lips that partially encompasses the smaller feeding tube assembly 20. However, in other embodiments, the gastrostomy tube 10 may completely encompass the feeding tube assembly 20. In certain embodiments, the feeding tube assembly 20 has a generally elliptical cross section. In other embodiments, the cross section of the feeding tube assembly 20 may be irregular. More generally, the cross section of the feeding tube assembly 20 may be non-circular. When the cross-section of the feeding tube assembly 20 is non-circular, the assembly can be accommodated in a tube support channel having a corresponding shape which limits or prevents rotation of the feeding tube assembly relative to the gastrostomy tube 10. Advantageously, this restricted rotational movement reduces the chances of the feeding tube assembly becoming twisted and dislodged in a patient's stomach. When properly combined, the feeding tube assembly 20 is able to freely slide against the gastrostomy tube 10 through the space 29. In some embodiments, the gastrostomy tube 10 may include a releasable lock designed to restrict the sliding movement of the feeding tube assembly 20 within the space 29 and retain the assembly in position against the wall of the gastrostomy tube until the lock is released. In certain embodiments, the releasable lock is disposed on the proximal end 11 of the gastrostomy tube 10. This arrangement allows the gastrostomy tube 10 or feeding tube assembly 20 to be removed or adjusted as needed without the need to remove any other components of the bariatric device 1 by simply releasing the lock and sliding the relevant tube in and out of position. This makes installation of the bariatric device 1 easier and less invasive than prior art devices and methods. It also makes it easier to clean both the gastrostomy tube 10 and stoma through which the tube extends, since the gastrostomy tube 10 can be temporarily slid out of position to facilitate cleaning without disrupting the position of the feeding tube assembly 20. In the shown embodiment, the releasable lock is provided by the overhanging lips of the tube support channel, which "grip" the feeding tube assembly 20 when gastrostomy tube balloon 14 (discussed in relation to FIG. 2) is inflated. More specifically, to "lock" the feeding tube assembly 20 in place, the gastrostomy tube balloon 14 is inflated so as to create a constrictive force which squeezes the overhanging lips of the tube support channel towards one another and thus causes the tube support channel to "grip" the feeding tube assembly 20. To "unlock" the feeding tube assembly 20 the gastrostomy tube balloon 14 is (at least partially) deflated so as to cause the overhanging lips of the tube support channel to relax and loose their grip. Stated more generally, the releasable lock may be provided by a deformable jaw on the tube support channel which grips the feeding tube assembly when the gastrostomy tube is inflated.

Figure 2:
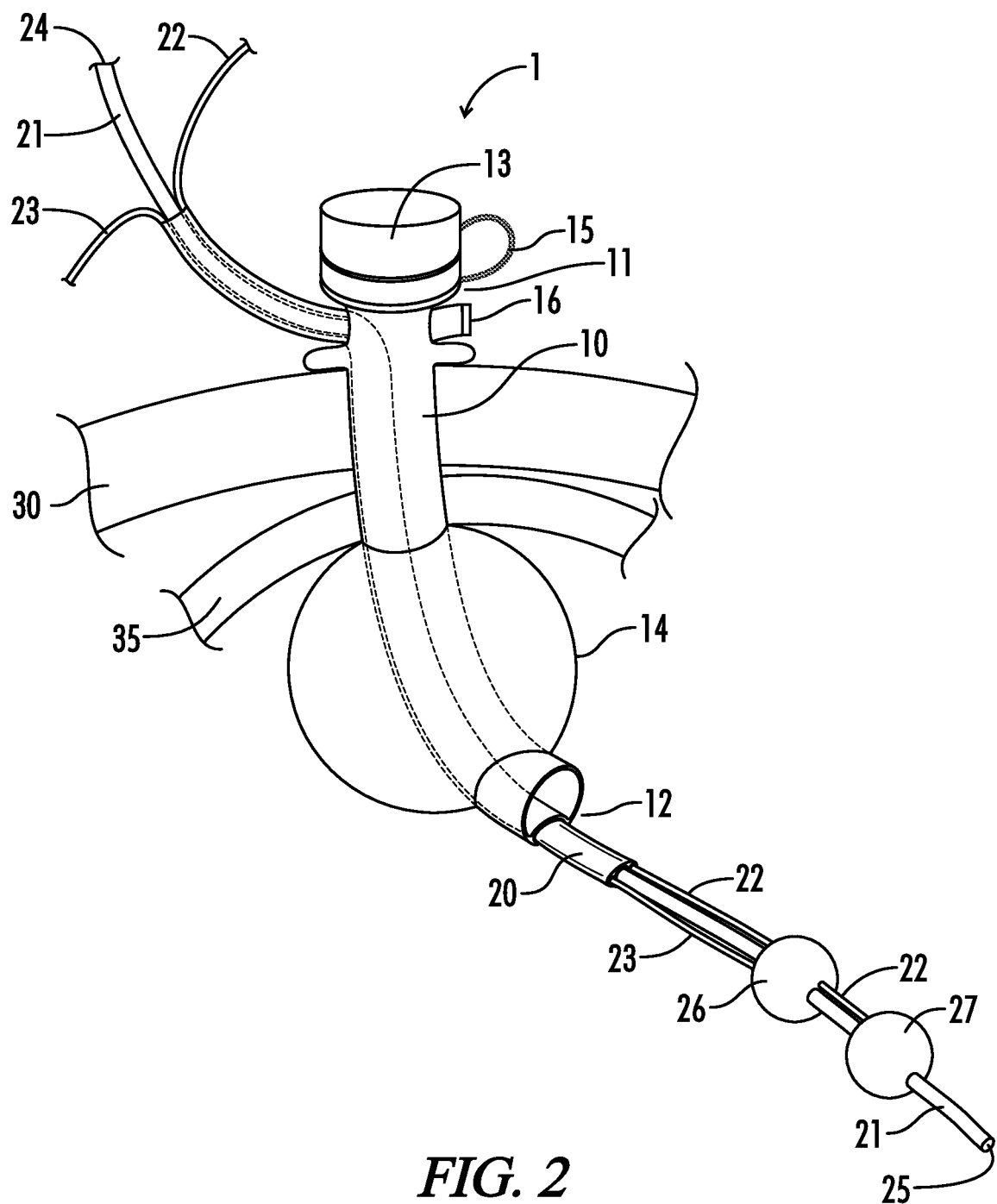
FIG. 2 is a diagram illustrating the bariatric device of FIG. 1 anchored in the stomach of a human being.

Referring now to FIG. 2, there is illustrated a diagram of a trans-abdominal bariatric device 1 installed in a person with the gastrostomy tube 10 and nested feeding tube assembly 20 extending through the abdominal wall 30 and stomach wall 35. The gastrostomy tube 10 further comprises a distal end 12 and a proximal end 11. The proximal end 11 is disposed outside the patient's abdominal wall 30 and comprises a lid 13 for sealing the proximal end 11 and a closeable button 15. The button 15 is an outlet which may be connected to a vacuum pump for mechanically evacuating by suction the contents of a person's stomach into an attached disposable bag or other receptacle for disposal. The distal end 12 of the gastrostomy tube 10 remains open to and is disposed in the person's stomach. The distal end 12 is also attached to a gastrostomy tube balloon 14 for anchoring the gastrostomy tube 10 in position on the inside of the stomach. The balloon 14 can be inflated through a gastrostomy tube balloon inflation tube (not shown) using the access point 16 located on the proximal end 11 of the gastrostomy tube 10 between the lid 13 and the abdominal wall 30. The balloon 14 may be filled with liquid or gas, such as air, water or saline, which is moved through the inflation tube (not shown) into the balloon 14. The gastrostomy tube balloon 14 may be inflated during installation or afterwards.

The nested feeding tube assembly 20 is attached to and extends beyond the distal end 12 of the gastrostomy tube 10 into the patient's duodenum. Like the gastrostomy tube 10, the feeding tube 21 has a distal end 25 and a proximal end 24, the proximal end 24 being located outside the abdominal wall 30 and sealed by a removeable cap. The distal end 25 terminates in and remains open to the person's duodenum, and is held in position by two feeding tube balloons 26, 27, including a distal balloon 27 and a proximal balloon 26. The proximal balloon 26 is located before the pyloric sphincter and the distal balloon 27 is located after the pyloric sphincter. In the embodiment shown in the figure, the balloons 26, 27 take the form of inflatable sleeves completely surrounding and integrally formed with the feeding tube 21. To prevent occlusion of the feeding tube 21 by the pressure of the inflated balloons 26, 27, the sections of the feeding tube 21 inside balloons 26 and 27 are made relatively stiffer than other sections of the feeding tube 21. This can be achieved, for example, by making the sidewalls of the feeding tube 21 relatively thicker in these sections, selecting a different material for these sections, and/or by subjecting these sections to a stiffening treatment. In other embodiments, the balloons 26, 27 may only partially surround the feeding tube 21, for example, each balloon may take the form of one or more inflatable cells or pockets distributed around the feeding tube 21. Although the balloons 26, 27 are formed integrally with the feeding tube 21 in the shown embodiment, it will be appreciated that in other embodiments the balloons 26, 27 may be separately formed from the feeding tube 21, for example, each balloon 26, 27 may be a separate balloon attached to the feeding tube 21. In such embodiments, the balloons 26, 27 may be movable (e.g. slidable) relative to the feeding tube 21 over a limited range (e.g. so as to allow a single design to be adapted to suit different patients). For example, one or both balloons 26, 27 may take the form of an inflatable sleeve which the feeding tube can be threaded through, with the sleeves optionally held in position relative to the feeding tube by the constrictive force created when the balloons 26, 27 are inflated.

Each balloon 26, 27 is in communication with and is inflatable via one of the inflation tubes 22, 23, which may be connected to an external balloon inflation control device (not pictured). It will be appreciated that in alternative embodiments both balloons can be inflated via a single inflation tube. The balloon inflation tubes 22, 23 are disposed parallel to the feeding tube 21 within the feeding tube assembly 20, and each extends from outside the abdominal wall 30 to a respective balloon 26, 27. When the feeding tube balloons 26, 27 are inflated, they anchor/secure the feeding tube assembly 20 relative to the pyloric sphincter. In one embodiment, there is at least one feeding tube balloon anchoring the feeding tube assembly 20. However, there may be two feeding tube balloons anchoring the feeding tube assembly, one on either side of the pyloric sphincter, so as to restrict forward and backward movement of the feeding tube through the pyloric sphincter.

Generally, in embodiments having two feeding tube anchors, said anchors are separated by a distance of less than 15 cm, less than 12 cm, less than 10 cm, less than 8 cm, less than 6 cm or less than 4 cm. For example, the feeding tube anchors may be separated by between about 1 to about 15 cm, between about 1 to about 10 cm, or between about 1 to about 5 cm. Advantageously, spacing the feeding tube anchors by this distance allows only a limited amount of movement of the feeding tube back and forth through the pyloric sphincter, which helps to prevent the feeding tube assembly from becoming dislodged. In the embodiment shown in the figures, the distance separating the balloons is the distance measured between the outer surfaces of balloons 26 and 27 at their point of closest approach.

Figure 5:
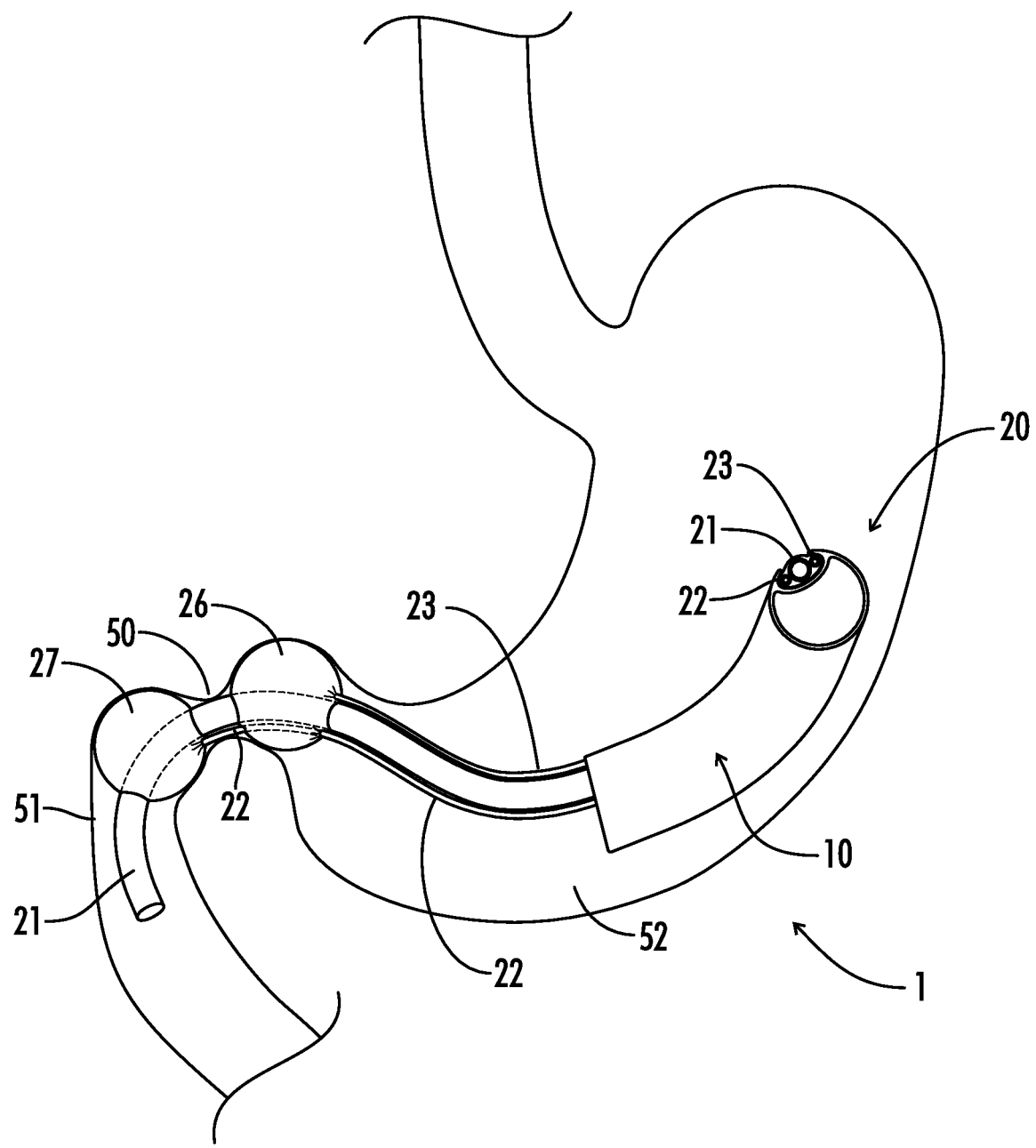
FIG. 5 is a diagram illustrating an internal view of the bariatric device of FIG. 1 installed in the stomach of a human being.

When fully expanded the first and/or second feeding tube anchors may have a width of at least 5 mm, at least 10 mm, at least 12 mm, at least 15 mm, at least 18 mm, at least 20 mm, at least 22 mm, or at least 25 mm. For example, the feeding tube anchors may have a width of between 10 and 25 mm, or between 15 and 25 mm. Advantageously, feeding tube anchors having these dimensions are wider than the diameter of the pyloric sphincter in the sphincter's open position, meaning that the positioning of the feeding tube is not affected by pyloric contractions. At least one feeding tube anchor may be sufficiently wide in its fully expanded state to substantially or completely occlude the duodenum. Such a situation is shown in FIG. 5, where feeding tube balloons 26 or 27 occlude the duodenum 51 in their inflated states. This prevents the passage of stomach contents to the duodenum 51, meaning that orally-ingested food and stomach phlegm can be aspirated from the stomach through gastrostomy tube 10 without the need to aspirate further down the digestive tract. Consequently, this provides a way of controlling the amount of food reaching the lower digestive tract.

Suitably, the gastrostomy tube 10 does not enter the duodenum 51. As a result, the gastrostomy tube 10 can be made relatively shorter and wider than the feeding tube assembly 20, since it is not necessary for the gastrostomy tube to fit within the narrow duodenum 51. As described above, the relatively large diameter of the gastrostomy tube 10 reduces the propensity of the gastrostomy tube to become clogged during aspiration. Suitably, the length of the gastrostomy tube 10 which is within the body in use may be less than 75%, less than 50%, less than 40% or less than 30% of the length of the feeding tube 21 which is within the body in use. By "length of the gastrostomy tube which is within the body in use" we mean the length as measured from the part of the gastrostomy tube 10 which abuts the patient's stomach wall 35 in use (e.g. the outer surface of a fully-inflated gastrostomy balloon closest to the proximal end 11 of the gastrostomy tube) to the distal end 12 of the gastrostomy tube 10. By "length of the feeding tube which is within the body in use" we mean the length as measured from the part of the gastrostomy tube which abuts the patient's stomach wall 35 in use to the distal end 25 of the feeding tube 21.

To remove the gastrostomy tube 10, the gastrostomy balloon 14 is deflated and the gastrostomy tube 10 is slid off of the feeding tube assembly 20. A further gastrostomy tube can then be installed by sliding the gastrostomy tube 10 onto and along the feeding tube assembly 20 until the correct position is reached. The feeding tube balloons 26 and 27 can remain inflated during this procedure, so as to retain the feeding tube 21 in its position within the duodenum 51, allowing the gastrostomy tube to be replaced in a minimally invasive way.

Similarly, to remove the feeding tube assembly 20, the feeding tube balloons 26 and 27 are deflated and the feeding tube assembly 20 is slid out of the gastrostomy tube 10. A further feeding tube assembly can then be installed by slotting the feeding tube assembly 20 through space 29 until the correct position is reached. If the device includes a releasable lock holding the feeding tube assembly 20 in place, the lock should be released before removal of the feeding tube assembly 20 from the gastrostomy tube 10. For example, in the shown embodiment, the gastrostomy balloon 14 is partially deflated so as to allow the feeding tube assembly 20 to be removed whilst still securing the gastrostomy tube 10 in position, allowing the feeding tube assembly 20 to be replaced in a minimally invasive way.

Figure 3:
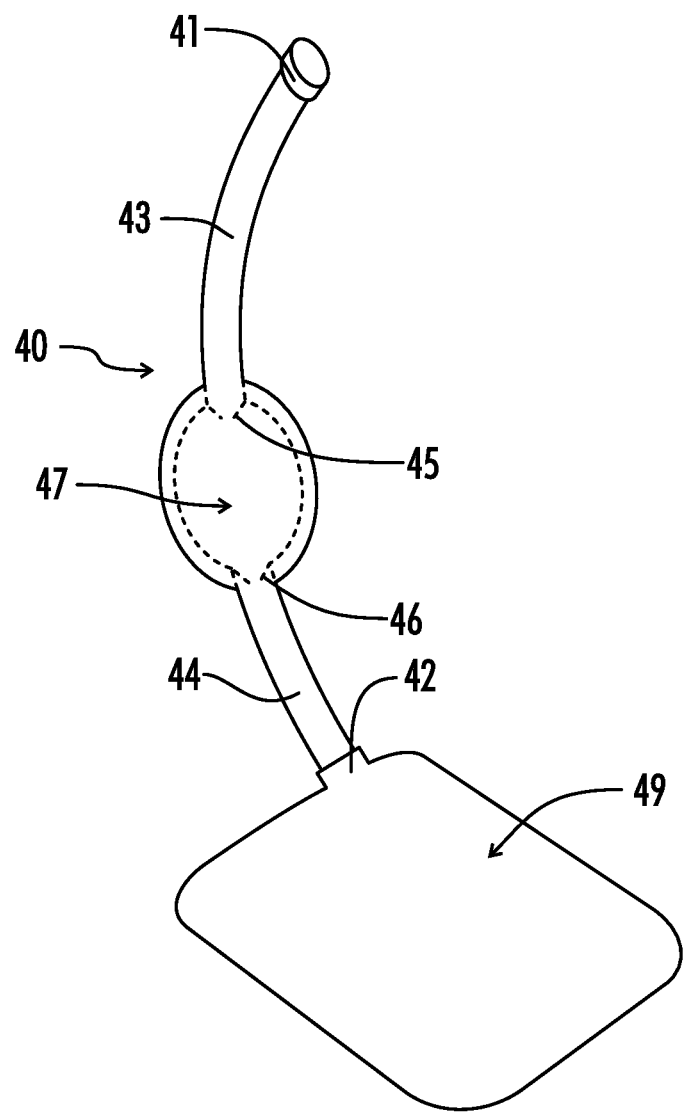
FIG. 3 is a diagram illustrating a pump that can be attached to the bariatric device of FIG. 1 to evacuate food from a person's stomach through the gastrostomy tube.

Referring now to FIG. 3, there is illustrated a diagram of a manual hand pump 40 and a releasably attached disposable bag 49 suitable for use with the trans-abdominal bariatric device 1 of FIG. 1. The pump 40 comprises a squeezable bulb 47 having an inlet valve 45 and an outlet valve 46; an inlet tube 43; and an outlet tube 44. The bulb 47 is connected to one end of the inlet tube 43 at the inlet valve 45, and one end of the outlet tube 44 at the outlet valve 46. The opposite end 41 of the inlet tube connects to the button 15 (see FIG. 2) of the gastrostomy tube 10 and the opposite end 42 of the outlet tube connects to a disposable bag 49. When connected to the bariatric device 1 and a disposable bag 49, a person may squeeze or compress the bulb 47 to suction food out of the stomach and into the bag 49. When full, the disposable bag 49 may be disconnected from the outlet tube 44, discarded and replaced with a new bag as needed. The type of vacuum pump used may vary. Suitable pumps include manual as well as electric and battery powered pumps, and the like. The type of pump used should provide suction strong enough to evacuate thick or viscous consumed food from the stomach, but not so strong as to damage tissue or organs.

Figure 4:
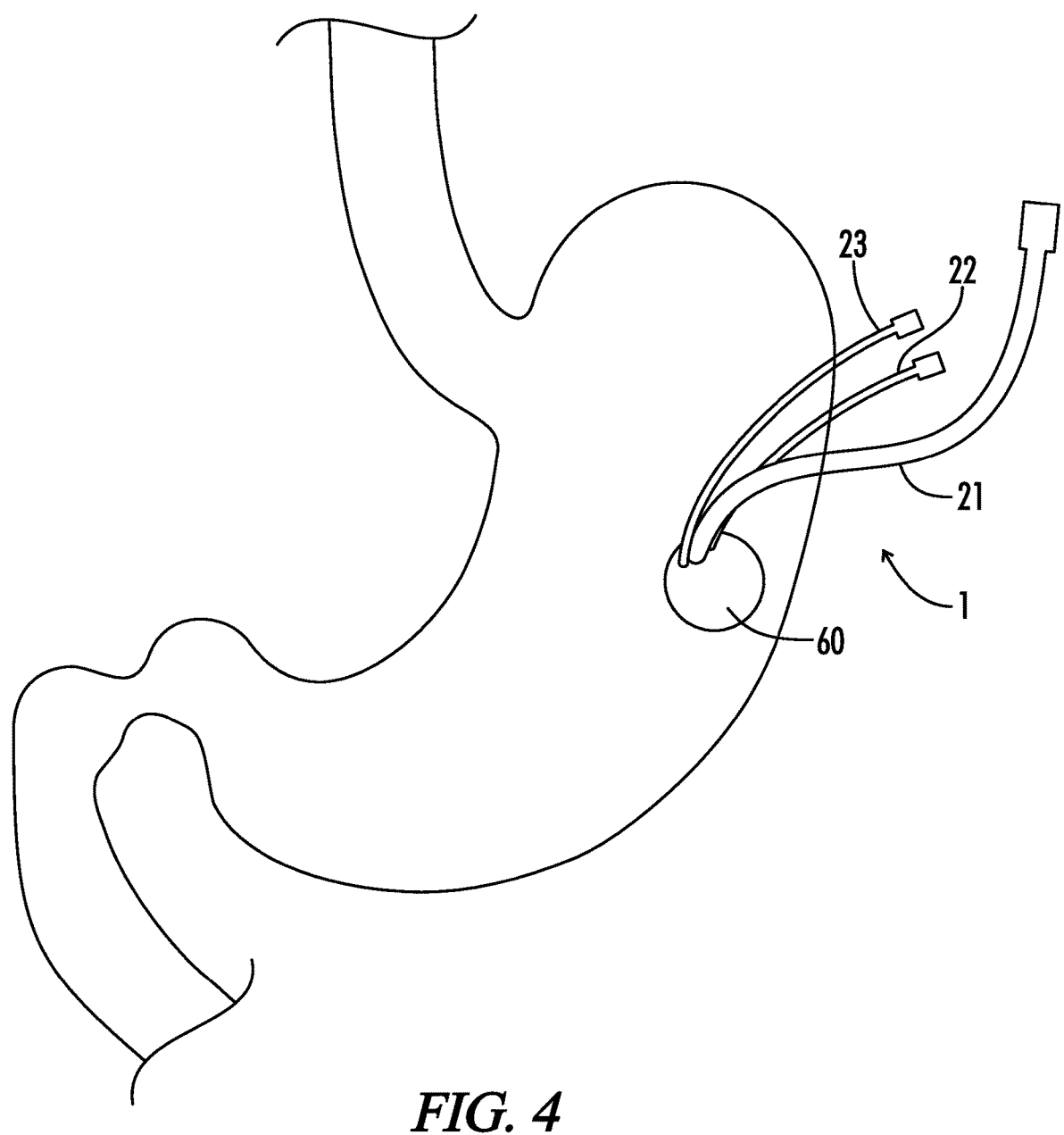
FIG. 4 is a diagram illustrating an external view of the feeding tube assembly of the bariatric device of FIG. 1 installed in the stomach of a human being.

Referring now to FIG. 4, there is provided a diagram illustrating a simplified external view of the feeding tube assembly of the bariatric device of FIG. 1 installed in the stomach of a human being. The feeding tube assembly 20 extends through the abdomen from outside the body to inside the stomach via a gastrostoma. The point of entry is sealed by a patch 60 through which the feeding tube assembly 20 extends. The feeding tube 21 through which controlled feeding is performed extends from the patch 60 to a point outside the body. The exposed length of feeding tube 21 may be adjusted to suit the person in which it is installed. Also extending outwardly from the patch 60 (outside the body) are the proximal ends of the two balloon inflation tubes 22, 23. These may be connected to a balloon inflation control (not shown), which can be used to selectively inflate the balloons.

Referring now to FIG. 5, there is provided a diagram illustrating an internal view of bariatric device of FIG. 1 installed in the stomach of a human being. A cross section of the bariatric device 1 is shown in place of the patch 60 of FIG. 4. The gastrostomy tube 10 and nested feeding tube assembly 20 pass through the abdomen and stomach wall. The gastrostomy tube 10 terminates in the stomach 52, while the feeding tube 20 and one balloon inflation tube 22 continues through the stomach 52 and pyloric sphincter 50 into the duodenum 51. The other balloon inflation tube, 23, terminates at the bottom of the stomach 52 at the pyloric sphincter 50. The feeding tube 21 terminates in the duodenum 51 and is attached to two feeding tube balloons, 26, 27, the proximal balloon 26 located before the pyloric sphincter and the distal balloon 27 located after the pyloric sphincter. Each balloon inflation tube 22, 23 is in communication with a feeding tube balloon 26, 27. Each feeding tube balloon, 26, 27 is disposed on either side of the pyloric sphincter 50. Inflation of the balloons via the balloon inflation tubes 26, 27 anchors the feeding tube 21 in the duodenum 50. To form a completed bariatric device 1, a user slots the feeding tube assembly 20 through the space 29 of a gastrostomy tube 10, and gently slides the gastrostomy tube 10 into position. Once in position, the gastrostomy balloon 14 of the gastrostomy tube 10 is inflated within the stomach, so as to anchor the gastrostomy tube 10 in place (as shown in FIG. 2).

Figure 6:
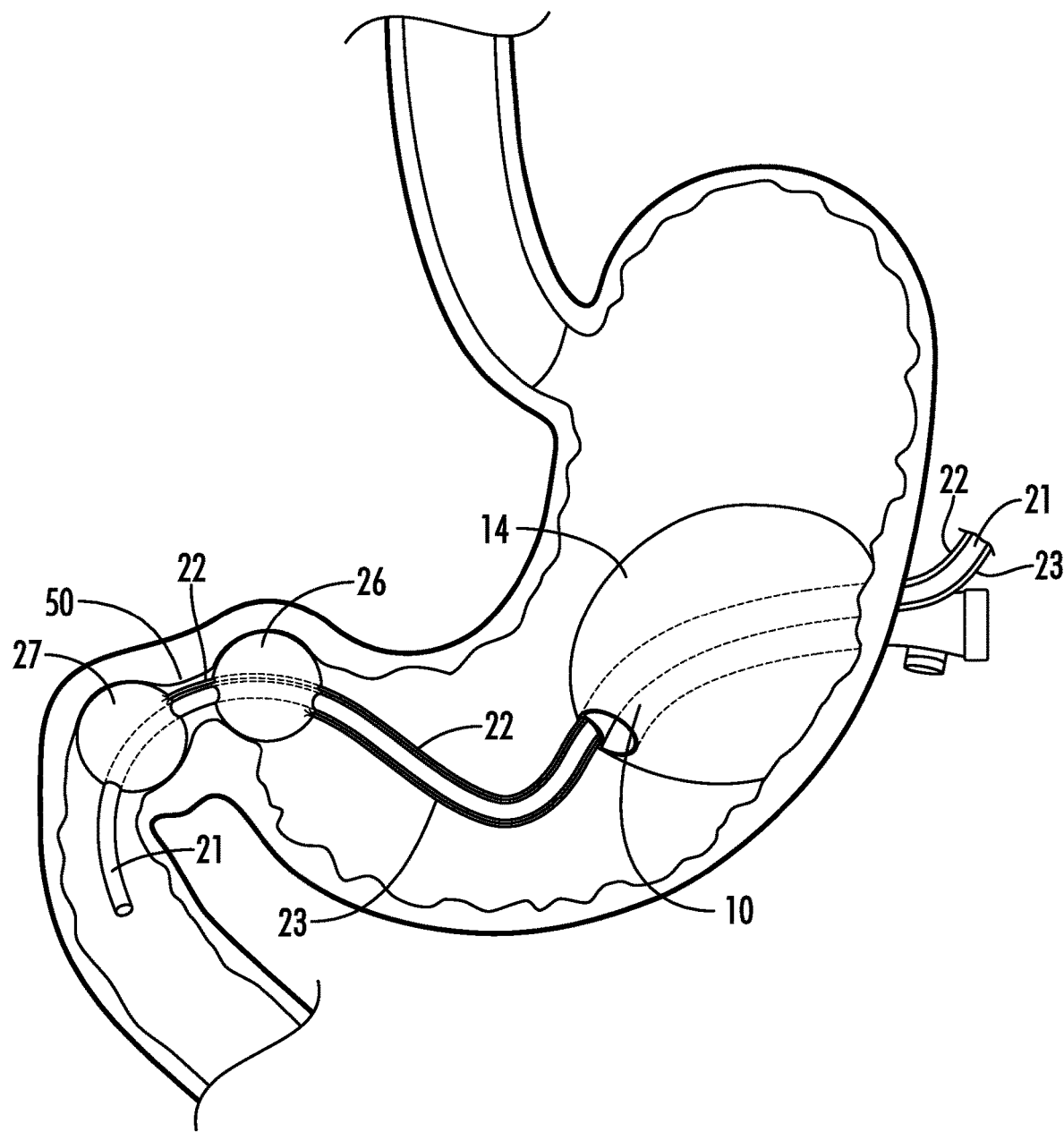
FIG. 6 is a further diagram illustrating an internal view of the bariatric device of FIG. 1 installed in the stomach of a human being.

Referring now to FIG. 6, there is provided an alternative view of the bariatric device 1 of FIG. 5 installed in a patient. The figure shows gastrostomy tube 10 anchored within a patient's stomach by gastrostomy balloon 14, and feeding tube 21 nested within gastrostomy tube 10 extending beyond the end of gastrostomy tube 10 into the duodenum. The feeding tube 21 is held in position by balloons 26, 27 which have been inflated on either side of the pyloric sphincter 50 via inflation tubes 22, 23.

Figure 7:
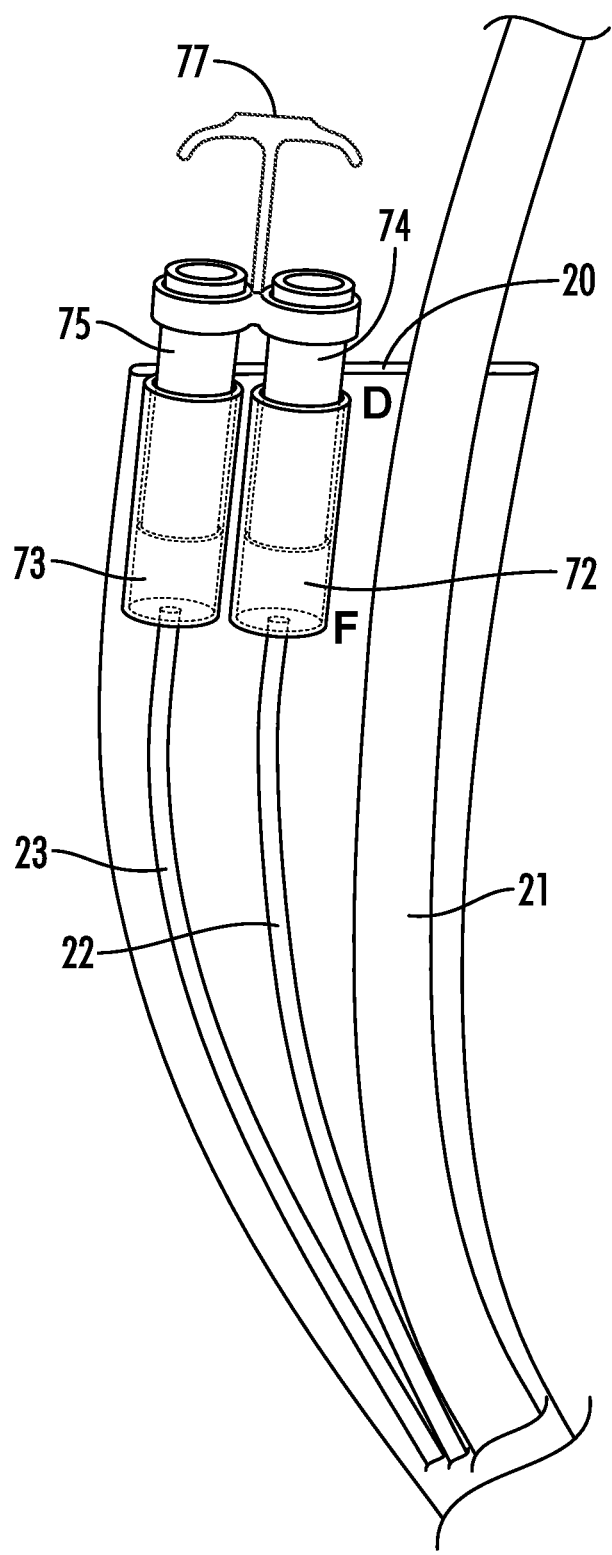
FIG. 7 is a diagram illustrating the proximal end of the feeding tube assembly.

Referring now to FIG. 7, there is provided a diagram of the proximal end of the feeding tube assembly 20, so as to illustrate how feeding tube balloons 26 and 27 are inflated. Inflation tubes 22 and 23 are shown connected to filling chambers 72 and 73 respectively, with the inflation tubes 22, 23 and filling chambers 72, 73 containing a balloon inflation fluid, in this case, a saline solution. Plungers 74 and 75 positioned within chambers 72 and 73 respectively are used to control the delivery of fluid from the chambers 72 and 73 to the feeding tube balloons 26 and 27 respectively. The plungers 74, 75 are both connected to a single handle 77, so as to allow the plungers to be compressed in a single movement. However, handle 77 can be removed to allow each plunger 74, 75 to be independently actuated (e.g. to deflate one balloon whilst the other remains inflated). In the embodiment shown, the plungers 74, 75 have been depressed from position D to position F so as to inflate the balloons 26 and 27 on either side of the pylorus so as to prevent stomach contents from passing to the intestines. To deflate balloons 26 and 27 the plungers 74, 75 can be lifted from position F to position D. In use, a patient may wish to allow delivery of some stomach contents to the intestines for short periods; for example, when taking medication or when drinking. To achieve this, the user can deflate balloon 26 by lifting plunger 74 and partially deflate balloon 27 by lifting plunger 75, thus allowing passage of the desired contents from the stomach into the intestines whilst the feeding tube 21 remains anchored in position. Once the desired contents have reached the intestines, the user can re-inflate balloons 26 and 27 by compressing plungers 74 and 75 again. This provides the user with good flexibility to control the material reaching their intestines.

Interpretation

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing an invention (especially in the context of the following claims) are to be construed to cover both the singular and the plural, unless otherwise indicated herein or clearly contradicted by context. The terms "comprising," "having," "including," and "containing" are to be construed as open-ended terms (i.e., "including, but not limited to,") unless otherwise noted. Recitation of ranges as values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention (i.e., "such as, but not limited to,") unless otherwise claimed. No language in the specification should be construed as indicating any non-claimed element as essential to the practice of the invention.

While the disclosure above sets forth the principles of the invention disclosed herein, with examples given for illustration only, those skilled in the art will appreciate from the foregoing that various adaptations and modifications of the just described embodiments can be configured in various respects without departing from the scope and spirit of the invention. The inventors expect that skilled artisans will employ various obvious changes in form and detail, and the inventors intend for the invention to be practiced other than as specifically described herein. Accordingly, the invention includes all equivalents and usual and obvious modifications of the subject matter recited in the claims appended hereto as permitted by applicable law. Moreover, any combination of the above-described features and elements in all possible variations hereof is encompassed by the invention unless otherwise indicated herein or otherwise clearly contradicted by context. Therefore, it is to be understood that the invention must be measured by the scope of the appended claims and not by the description of the examples or the preferred embodiments.

What is claimed is:

1. A bariatric device, comprising:
    a gastrostomy tube having a proximal end and a distal end, a protrusion on the proximal end, a support channel, an outside wall, and an anchor;
    a feeding tube assembly, said assembly including a feeding tube with a proximal end and a distal end;
    the gastrostomy tube anchor further comprising a gastrostomy balloon attached to said gastrostomy tube, wherein the gastrostomy balloon is designed to be expanded against the inside of a person's stomach at the stomach wall to secure the distal end of said gastrostomy tube inside the stomach by pressing against the protrusion on the proximal end of said gastrostomy tube outside the person's abdominal wall;
    the support channel of the gastrostomy tube configured to accommodate the feeding tube at least partially nested in the outside wall of the gastrostomy tube; and
    a first feeding tube anchor attached to said feeding tube assembly, said first feeding tube anchor designed to be expanded after a person's pyloric sphincter so as to secure the distal end of the feeding tube in a person's duodenum;
    wherein, when the feeding tube is in the support channel, the gastrostomy tube and the feeding tube pass through the gastrostomy balloon, which gastrostomy balloon is configured to constrict the support channel and hold the feeding tube against the gastrostomy tube when the gastrostomy balloon is inflated.

2. A bariatric device according to claim 1, wherein the first feeding tube anchor is a first feeding tube balloon designed to be inflated after a person's pyloric sphincter, and the feeding tube assembly includes a first balloon inflation tube, wherein the first feeding tube balloon is in communication with said first balloon inflation tube.

3. A bariatric device according to claim 1, further comprising a second feeding tube anchor attached to said feeding tube assembly, wherein said first and second feeding tube anchors are designed to be expanded on either side of a person's pyloric sphincter so as to anchor the distal end of said feeding tube in a person's duodenum.

4. A bariatric device according to claim 1, further comprising a second feeding tube anchor, wherein said first and second feeding tube anchors are designed to be expanded on either side of a person's pyloric sphincter so as to anchor the proximal end of said feeding tube in a person's duodenum.

5. A bariatric device according to claim 4, wherein the second feeding tube anchor is a second feeding tube balloon designed to be inflated before a person's pyloric sphincter, and the feeding tube assembly includes a second balloon inflation tube, wherein the second feeding tube balloon is in communication with said second balloon inflation tube.

6. A bariatric device according to claim 5, wherein the feeding tube assembly is at least partially nested on said gastrostomy tube.

7. A bariatric device according to claim 5, wherein the feeding tube assembly is slidably nested against said gastrostomy tube.

8. A bariatric device according to claim 1, wherein the tube support channel extends along 80% or more of the gastrostomy tube.

9. A bariatric device according to claim 1, wherein the cross-section of the feeding tube assembly is non-circular, and the tube support channel has a corresponding shape which limits or prevents rotation of the feeding tube assembly relative to the gastrostomy tube.

10. A bariatric device according to claim 5, wherein said first and second feeding tube balloons are separated by a distance of between 1 to 15 cm.

11. A bariatric device according to claim 5, wherein said first and second feeding tube balloons are separated by a distance of between 1 to 5 cm.

12. A bariatric device according to claim 5, wherein said first and second feeding tube balloons have a width of between 10 mm to 25 mm.

13. A bariatric device according to claim 5, wherein at least one of said first and second feeding tube balloons is sufficiently wide in its fully expanded state to occlude the duodenum in use.

14. A bariatric device according to claim 5, wherein the diameter of the gastrostomy tube is between 0.5 to 5.0 cm.

15. A bariatric device, comprising:
   a gastrostomy tube having a proximal end and a distal end, a support channel, an outside wall, and a gastrostomy balloon;
   a feeding tube assembly at least partially nested within said gastrostomy tube, said feeding tube assembly having a proximal end and a distal end and including a feeding tube and first and second balloon inflation tubes;
   the gastrostomy balloon attached to said gastrostomy tube and designed to be inflated and anchor the distal end of said gastrostomy tube inside a person's stomach wall against the proximal end of said gastrostomy tube outside a person's abdominal wall;
   the support channel of the gastrostomy tube configured to accommodate the feeding tube inset on the outside wall of the gastrostomy tube and configured to act as a lock on the feeding tube when the gastrostomy balloon is inflated with the feeding tube inside the support channel of the gastrostomy tube; and
   first and second feeding tube balloons in communication with said first and second balloon inflation tubes, said first and second balloons designed to be inflated on either side of a person's pyloric sphincter and anchor the distal end of said feeding tube in a person's duodenum.

16. A kit of parts for constructing a bariatric device according to claim 5, comprising a gastrostomy tube and a feeding tube assembly.

17. A method for reducing the weight of a person, comprising installing a bariatric device according to claim 1 in said person's stomach and limiting the amount of food that passes from the stomach into the duodenum using said device to evacuate orally consumed food and directly deposit nutrition to the person's intestinal tract downstream of the stomach.

18. A method for reducing the weight of a person for cosmetic purposes using a bariatric device according to claim 1, the method comprising limiting the amount of food that passes from the stomach into the duodenum using said device to evacuate orally consumed food and directly deposit nutrition to the person's intestinal tract downstream of the stomach.

19. A method for delivering nutrients to a person, comprising installing a bariatric device according to claim 1 in said person's stomach and using said device to evacuate orally consumed food and directly deposit nutrition to the person's intestinal tract downstream of the stomach.

20. A method for installing a bariatric device according to claim 1, comprising:
   (i) inserting said gastrostomy tube into the person's stomach and anchoring the gastrostomy tube in place by expanding said gastrostomy tube anchor; and
   (ii) inserting said feeding tube assembly through the person's stomach into the duodenum and securing said feeding tube in place by expanding said first feeding tube anchor after the pyloric sphincter.

21. A method for replacing a gastrostomy tube in a bariatric device according to claim 1, comprising:
   (i) retracting said gastrostomy tube anchor and removing said gastrostomy tube; and
   (ii) inserting a replacement gastrostomy tube having the features described in claim 1 and expanding the gastrostomy tube anchor of the replacement gastrostomy tube.

22. A method for replacing a feeding tube assembly in a bariatric device according to claim 1, comprising:
   (i) retracting said first feeding tube anchor and removing said feeding tube assembly; and
   (ii) inserting a replacement feeding tube assembly having the features described in claim 1 and expanding the first feeding tube anchor of the replacement feeding tube assembly.

\* \* \* \* \*